United States Patent [19]

Platz et al.

[11] 4,219,666
[45] Aug. 26, 1980

[54] PREPARATION OF CARBOXYLIC ACID ESTERS OF VICINAL GLYCOLS

[75] Inventors: Rolf Platz, Mannheim; Hans-Martin Weitz, Bad Durkheim; Juergen Hartig, Gruenstadt, all of Fed. Rep. of Germany

[73] Assignee: BASF Aktiengesellschaft, Fed. Rep. of Germany

[21] Appl. No.: 61,890

[22] Filed: Jul. 30, 1979

[30] Foreign Application Priority Data

Aug. 7, 1978 [DE] Fed. Rep. of Germany ....... 2834540

[51] Int. Cl.$^2$ .............................................. C07C 67/04
[52] U.S. Cl. .................................................. 560/246
[58] Field of Search ........................................ 560/246

[56] References Cited

U.S. PATENT DOCUMENTS

| | | | |
|---|---|---|---|
| 3,668,239 | 6/1972 | Kollar | 560/246 |
| 3,674,813 | 7/1972 | Bljumberg et al. | 560/246 |
| 3,985,795 | 10/1976 | Kollar | 560/246 |
| 4,000,185 | 12/1976 | Kurkov et al. | 560/246 |
| 4,045,477 | 8/1977 | Sherwin et al. | 560/246 |
| 4,069,381 | 1/1978 | Gaenzler et al. | 560/246 |
| 4,073,876 | 2/1978 | Gupta | 560/246 |
| 4,122,286 | 10/1978 | Hartig et al. | 560/246 |

FOREIGN PATENT DOCUMENTS 2632158  1/1977  Fed. Rep. of Germany .

*Primary Examiner*—Joseph E. Evans
*Attorney, Agent, or Firm*—Keil & Witherspoon

[57] ABSTRACT

Carboxylic acid esters of vicinal glycols are prepared by oxidizing olefins with oxygen in the presence of carboxylic acids and of halogen and tellurium salts as catalysts, the reaction being carried out in vessels and apparatus consisting of, or lined with, zirconium or alloys of not less than 80% by weight of zirconium, the remainder being tin and/or hafnium.

1 Claim, No Drawings

PREPARATION OF CARBOXYLIC ACID ESTERS OF VICINAL GLYCOLS

The present invention relates to an improved process for the preparation of carboxylic acid esters of vicinal glycols by catalytic oxidation of olefins with oxygen in the presence of carboxylic acids, in the liquid phase.

U.S. Pat. No. 3,985,795 and German Laid-Open Application DOS No. 2,632,158 disclose the conversion of olefins in the liquid phase, in the presence of halogens and tellurium salts, to carboxylic acid monoesters and diesters of the vicinal glycols corresponding to the olefins.

A particularly important embodiment is the reaction of ethylene and propylene with acetic acid in the presence of a halogen or halogen donor and in the presence of tellurium cations, at elevated temperature and under superatmospheric pressure, in accordance with the equation

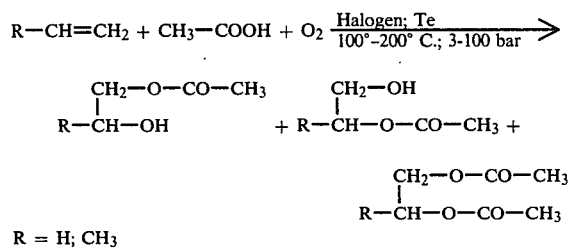

R = H; CH₃ since these esters can respectively be converted to ethylene oxide and propylene oxide, with elimination of acetic acid.

Though this reaction takes place with high spacetime yield and is, per se, a very advantageous step in the preparation of alkylene oxides, it has not hitherto found employment in industry. The acid reaction mixture, containing oxygen, halogen and tellurium salts, is so corrosive under the conditions of the process, that hitherto no corrosion-resistant material of construction, which would allow commercial utilization of this method of oxidation, has been found.

Steels, such as chromium-nickel-molybdenum steels which normally are corrosion-resistant even under rather severe conditions exhibit an unacceptable degree of corrosion after only a few operating hours, and even titanium itself proves not to be usable. Only tantalum has so far proved corrosion-resistant, but since this material is extremely expensive it can, for economic reasons, virtually not be considered for industrial plant.

It is an object of the present invention to provide a material of construction for reaction vessels and apparatus, in which the above process can be carried out without corrosion problems.

We have found that this object is achieved and that carboxylic acid esters of vicinal glycols may be prepared by liquid phase oxidation of olefins with oxygen in the presence of carboxylic acids and of halogens and tellurium salts as catalysts, without technological difficulties resulting from corrosion, if the reaction is carried out in vessels and apparatus which consist of, or are lined with, zirconium or alloys of not less than 80% by weight of zirconium, the remainder being tin and/or hafnium.

The use, according to the invention, of zirconium or zirconium alloys is in general advisable for those reaction mixtures, according to the general definition, which in addition to the non-corrosive starting materials, ie. the olefins, and the products, ie. the esters, contain the following amounts of corrosive substances: 40–95% by weight of a carboxylic acid, 0.5–10% by weight of halogen, eg. chlorine, bromine and/or iodine, in the elementary and/or ionic form, 0.05–5% by weight of tellurium dioxide or the equimolar amount of a tellurium salt, eg. a halide, and 0.002–0.3% by weight of oxygen, corresponding to an oxygen partial pressure of about 0.5–20 bar.

Where the oxidation reaction concerns the preparation of ethylene glycol acetate and propylene glycol acetate, which was mentioned at the outset and is industrially of particular importance, the above type of reaction mixture comprises 40–95% by weight of acetic acid, 0.5–10% by weight of halogen, especially iodine, 0.05–5% by weight of tellurium dioxide, 0.002–0.3% by weight of oxygen, corresponding to an oxygen partial pressure of 0.5–20bar, 1–5% by weight of water, 3–20% by weight of the olefin and 2–55% by weight of the ester mixture constituting the product.

Up to 180° C. and a pressure of 80 bar, no significant corrosion phenomena are observed, so that even under still more severe conditions an abrupt increase in corrosion is not to be expected. In general, however, there are probably no advantages in carrying out the oxidation reaction above 180° C. and 80 bar.

Compared to conventional materials, eg. chromium-nickel-molybdenum steels or titanium, zirconium and the zirconium alloys defined above offer substantial advantages even at 110° C. and 3 bar, ie. at the lower limits of the conditions under which the oxidation reactions are carried out industrially.

Zirconium and its alloys are conventional materials of construction and can be converted to reaction vessels and apparatus of all kinds by conventional methods. The same is true of linings, ie. of composite materials such as zirconium on steel. Normally, commercial zirconium contains about 5% by weight of its natural concomitant, hafnium, and it is only for special purposes that the hafnium is removed entirely or partially. For the purposes of the present invention, pure zirconium, which is more expensive, is of course suitable, but offers no advantages compared to hafnium-containing zirconium.

The great suitability of zirconium and its alloys for the purposes of the invention must be regarded as particularly remarkable in view of the fact that titanium, which in its chemical properties is very similar, cannot be used. Hitherto, only tantalum has been shown to be equally corrosion-resistant. However, the cost of tantalum apparatus is about three times as high as that of zirconium apparatus.

EXAMPLE

Material samples (each comprising one weld) of
A. a commercial zirconium sheet containing 4.5% by weight of hafnium,
B. a commercial sheet of an alloy containing about 94% by weight of zirconium, 4% by weight of hafnium and 2% by weight of tin,
and, for comparison,
C. a commercial tantalum sheet and
D. a commercial titanium sheet
were subjected to a conventional corrosion test in a model reaction mixture comprising 1,000 g of acetic acid, 200 g of a mixture of propanediol monoacetates and diacetate, 15 g of water, 25 g of iodine and 7 g of tellurium dioxide by heating for 30 days in an oxygen atmosphere, whilst stirring, at (a) 118° C. and, parallel thereto, (b) at 180° C.

At 118° C., the pressure was 1 bar, corresponding to an oxygen content of about 1 g in the reaction mixture, whilst at 180° C. the pressure was 25 bar, corresponding to an $O_2$ partial pressure of about 20 bar or an oxygen content of about 16 g in the mixture.

The material losses found were converted to a corrosion rate of mm/year.

The results are shown in the Table which follows.

| Material | Corrosion in mm/year | |
|---|---|---|
|  | at 118° C. | 180° C. |
| A Zirconium/(Hf) | 0.004 | 0.004 |
| B Zr/(Hf)/Sn | 0.018 | 0.036 |
| C Tantalum | 0.001 | 0.001 |
| D Titanium | 0.24+ | 10.7+ |

The results speak for themselves, and it is to be borne in mind that materials with surface corrosion rates of up to 0.1 mm/year are to be regarded as very suitable.

We claim:

1. A process for the preparation of carboxylic acid esters of vicinal glycols by oxidizing olefins with oxygen in the presence of carboxylic acids and of halogen and tellurium salts as catalysts, wherein this reaction is carried out in vessels and apparatus consisting of, or lined with, zirconium or alloys of not less than 80% by weight of zirconium, the remainder being tin and/or hafnium.

* * * * *